United States Patent [19]

Rutherford et al.

[11] Patent Number: 4,772,464

[45] Date of Patent: Sep. 20, 1988

[54] PROTECTIVE ANTIBODIES TO SEROTYPIC DETERMINANTS OF FLAGELLAR ANTIGENS

[75] Inventors: Richard L. Rutherford, San Rafael; Michael S. Collins, Richmond; Richard C. Harmon, Walnut Creek, all of Calif.

[73] Assignee: Miles Laboratories, Inc., Elkhart, Ind.

[21] Appl. No.: 761,737

[22] Filed: Aug. 1, 1985

[51] Int. Cl.$^4$ .................. C07K 15/04; A61K 39/395
[52] U.S. Cl. ........................................ 424/87; 530/387; 435/29; 435/240.27; 435/7; 935/104; 935/107; 935/110
[58] Field of Search .................. 530/387, 388; 435/68, 435/70, 172.2, 240, 241, 4, 7, 29, 32, 34, 259, 820, 873, 243, 253, 245; 424/87; 935/104, 106–108, 110; 436/548, 821

[56] References Cited

U.S. PATENT DOCUMENTS 4,443,549 4/1984 Sadowski ........................ 436/548
4,652,488 3/1987 Sadowski ........................ 424/87

FOREIGN PATENT DOCUMENTS 2192185 1/1988 United Kingdom .

OTHER PUBLICATIONS

Ueki, Y. et al, Microbiol. Immunol. 31(12): 1161–1171 (1987).
Anderson, T. R. et al, Infect. Immun. 55(12): 3204–6 (1987).
Drako, D. et al, J. General Microbiology 134: 43–52 (1988).
Torian, B. E. et al, Infect. and Immun., 43(1): 270–275 (1984) (cited in Chem. Abstract CA 100(9): 66320u).
Torian, B. E. et al, Infect. Immun., 46(1): 152–158 (1984) (cited in Chem. Abstract 101(19): 168705m).

*Primary Examiner*—Margaret Moskowitz
*Attorney, Agent, or Firm*—James A. Giblin

[57] ABSTRACT

Monoclonal antibodies specific to serotypic determinants on the flagella of a microorganism and found to be useful in inhibiting motility.

3 Claims, No Drawings

PROTECTIVE ANTIBODIES TO SEROTYPIC DETERMINANTS OF FLAGELLAR ANTIGENS

BACKGROUND OF THE INVENTION

1. Field

This disclosure is concerned generally with the field of monoclonal antibodies and specifically with the creation and use of an immortal cell line for the continuous production of antibodies found to be specific to serotypic determinants found on the flagella of microorganisms such as bacteria.

2. Prior Art

Since the early article by Köhler and Milstein, "Continuous Cultures of Fused Cells Secreting Antibody of Predefined Specificity", Nature 256:495–497 (1975), the production of monoclonal antibodies has become well known using both somatic cell hybrids (see, for example, U.S. Pat. No. 4,172,124 to H. Koprowski et al) or transformed cells (see, for example, U.S. Pat. No. 4,446,465 to M. Lostrom). In addition, there have been numerous patent disclosures concerned with the production of a wide variety of monoclonal antibodies and their uses, especially in diagnostic tests such as immunoassays (see, for example, U.S. Pat. No. 4,192,917 to Zurawski and U.S. Pat. No. 4,361,549 to Kung et al), purification (see, for example U.S. Pat. No. 4,361,509 to Zimmerman et al) and potential therapy (see, for example, U.S. Pat. No. 4,172,124 to Koprowski et al and U.S. Pat. No. 4,271,145 to Wands et al). For examples of early work on human monoclonal antibodies see, for example, International Patent Application No. PCT/US 81/00957, International Publication No. WO 82/01461, of Kaplan et al.

Although the technical and patent literature is now replete with many techniques involving the manufacture, modification or use of monoclonal antibodies of many different specificities, including bacterial pili which act as adhesions between prokaryotic and eukaryotic cells (see U.S. Pat. No. 4,443,549) and the flagella of sea urchin spermatozoa (see D. J. Asai et al, *Cell Motility* 2 Suppl. 1, 175–180, 1982), we are unaware of disclosures directed to the manufacture and use of protective monoclonal antibodies to serotypic determinants found on the flagella of motile microorganisms such as bacteria, algae, protozoans and the like. Quite surprisingly, we have now found that such monoclonal antibodies can be produced and characterized. More importantly, we have found that such monoclonal antibodies can be used for in vivo inhibition of motility of pathogenic microorganisms thus demonstrating a protective effect. Details of our findings are described herein.

SUMMARY OF THE INVENTION

The monoclonal antibodies of this disclosure are specific to serotypic determinants found on the flagella of unicellular microorganisms such as bacteria and algae. This disclosure is specifically directed to antigenic determinants on antigens associated with flagellated motile prokaryotes such as gram negative bacteria, especially of the Enterobacterioceae, Bacteroidaceae Pseudomonadoceae, Spirochaetaceae, Spirillaceae and Vibrionacene families. The antibodies are capable of inhibiting the motility of such organisms upon contact and can be derived from a clone which, in one embodiment, is produced hybridomally using immunologically active mammalian spleen cells and standard cell fusion procedures. The disclosure is illustrated below using a hybridoma clone to produce monoclonal antibodies specific to serotypic determinants of the flagella of *Proteus mirabilis* bacteria. Inhibition of the motility of that organism is also described. In experimental infection, the motility-inhibiting antibodies of this disclosure are highly protective.

SPECIFIC EMBODIMENTS

The monoclonal antibodies of the Examples were derived using a standard fusion procedure (Harmon et al, *Prog. Cancer Res. Ther.* 21, 21–30, 1982) using mouse spleen cells after active *P. mirabilis* immunization. The cell line used in the Example (our designation PM-5 VIII-4-F) has been deposited on July 30, 1985 with the American Type Culture Collection (ATCC), Rockville, Md. as Accession No. HB 8879.

The significance of using polyclonal antibodies for inhibiting motility of *P. mirabilis* is already well known (see, for example, McManus et al, "Experimental *Proteus mirabilis* Burn Surface Infection", Arch. Surg., Vol. 117, p. 187–191, 1982). See also, the article by G. Pazin et al, "Prevention of Ascending Spread of *Proteus mirabilis*", Investigative Urology, Vol. 12, No. 2 pp. 129–133, 1974. Further, the association of microorganism motility with virulence in *Pseudomonas aeruginosa* has been described by Holder et al in "Flagellar Preparations from *Pseudomonas aeruginosa:* Animal Protection Studies", Infection and Immunity, Vol. 35, No. 1, p. 276–280, January 1982.

*Proteus mirabilis* is a frequent cause of nosocomial infection and most commonly is isolated from the urinary tract and less frequently from wounds, burns, eyes, etc. *P. mirabilis* possesses numerous peritrichous flagella and is highly motile in liquid and soft agar media. Motility is a virulence factor, and non-motile mutants of *P. mirabilis* are much less virulent in experimental burn wound sepsis than motile parent strains (See McManus et al, above).

DEFINITION OF TERMS

As used herein, microorganism means a unicellular organism, especially prokaroyotic bacteria.

Flagellum (plural flagella) means a specialized locomotor organele comprising a filiform extention through the cell surface, occasionally bounded by an extension of the cytoplasmic membrane and comprising a single hellically bound filiment (commonly about 140 Å wide) and meant to include the periplasmic fibril of spirochetes. Flagella account for translocation of certain microorganisms.

The term motile means swimming or swarming due to the presence of flagella.

Inhibition of motility means the absence of motility to the extent that pathogenicity of a motile pathogenic microorganism is limited or eliminated.

Protective means capable of reducing cumulative mortality in infected animals or capable of limiting dissemination of a pathogenic organism from a site of primary infection or colonization.

Pathogenic means capable of causing infection in a suitable host.

Serotypic determinant means an antigenic structure, capable of being recognized by certain antibodies, which is variable among isolates of a given species and can therefore be used to distinguish such isolates.

Clone means a population of cells derived from a single cell and selected on the basis of production of a certain antibody.

PREPARATION OF CELL LINE

Bacterial Strains Used. Bacterial isolates used for immunization or to screen for the presence and specificity of antibody in hybridoma culture supernatants included a clinical wound isolate of Proteus mirabilis (our designation of strain number 4550ATCC number 53509), P. mirabilis ATCC numbers 12453, 25933, and 7002, P. vulgaris ATCC numbers e13315, 6380, 33420, and 8427, Providencia stuartii ATCC numbers 33672 and 35031, Morganella morganii ATCC number 25830, Yersenia enterocolitica ATCC number 23715, Escherichia coli ATCC number 8739, Aeromonas hydrophilia ATCC number 7966, Salmonella typhimurium SL1102 rFaE, Pseudomonas aeruginosa Fisher immunotype 2 ATCC number 27313, a Fisher immunotype 1 isolate of P. aeruginosa (obtained from Dr. J. A. Bass, Shriner's Hospital for Crippled Children, Galveston, Tex.), and an isolate representative of Bacillus subtilis.

Immunization of mice. Two female BALB/c mice received primary intraperitoneal immunizations at 7–9 weeks of age with 0.1 ml of a suspension of P. mirabilis 4550 cells. Secondary intraperitoneal and tertiary intravenous immunizations were with 0.1 ml of a suspension of P. mirabilis 4550 cells at days 21 and 42 following primary immunization, respectively. Secondary and tertiary immunizations were made with cell suspensions yielding an optical density at 660 nm of 0.1, while primary immunizations were made with a 1:10 dilution of such a suspension. All suspensions and dilutions were made in phosophate buffered saline (PBS). Spleens were harvested for fusion three days following tertiary immunization.

Cell fusion. For the production of the monoclonal antibodies, M5 cells, derived from a horse serum-adapted line of SP2/0-Ag14 (Shulman et al., Nature 276, 269–270, 1978), were grown in Dulbecco's Modified Eagle's Medium (DMEM, Gibco Laboratories, Grand Island, N.Y.) supplemented with 10% agamma horse serum (VSP horse serum, Biocell Laboratories, Carson, Calif.), 20 mM HEPES, 100 IU/ml penicillin, 100 μg/ml streptomycin and MEM nonessential amino acids. The fusion and culturing techniques were basically those of Kohler and Milstein (Nature 256, 495–497, 1975) with minor modifications (Harmon et al., Prog. Cancer Res. Ther. 21, 21–30, 1982). Fusion PM-5 was initiated with 34% (v/v) polyethylene glycol, MW 1,500 (Aldrich Chemical Co., Milwaukee, Wis.), at a ratio of 3 immunized splenocytes to 1 myeloma cell while fusion PM-6 was initiated under similar conditions except that the polyethylene glycol solution contained 5% dimethylsulfoxide. The fusion mixture was distributed into 96 well plates at approximately $3 \times 10^5$ spleen cells/0.2 ml HAT medium/well. Positive culture wells were selected on the basis of ELISA reactivity with P. mirabilis 4550 lysates and clonal hydridoma populations producing the antibodies of interest were isolated by limiting dilution culture and ELISA. After clones had been established, they were expanded by growth in supplemented DMEM and by ascitic growth in BALB/c mice which had been primed with pristane. Clarified tissue culture supernatant and/or ascites fluids were used as the source of antibodies for all of the assays described below.

Enzyme-linked immunosorbent assay (ELISA). Antibodies were detected using antigen-coated, round-bottom polystyrene 96 well microtiter plates (Immulon 2, Dynatech Laboratories, Alexandria, Va.). Wells were coated with 50 μl of one of three bacterial antigen solutions: lysate, whole cell or lipopolysaccharide (LPS). Bacterial lysates were prepared by sonication and diluted to optical density=0.025 at 280 nm in 50 mM sodium carbonate/bicarbonate buffer, pH 9.6. Coated plates were incubated for 3 hours at 37° C. before wells were washed with PBS and filled with 1% bovine serum albumin (BSA). The plates were then incubated for 1 hour at 37° C. prior to storage at −20° C. LPS-coated plates were prepared by adding 50 μl/well of a 10 μg/ml solution in carbonate buffer. The LPS preparations were obtained by hot phenol extraction (Westphal et al., Z. Naturforsch. 79, 148–155, 1952). LPS plates were incubated, blocked with BSA and stored as described above. Formalin-killed bacteria were suspended in PBS to an optical density of 0.123 at 660 nm for preparation of whole cell plates. 50 μl of whole cell suspension were added to wells before centrifugation of the plates at approximately 550 g for 20 minutes. The PBS was then removed from the wells and plates were incubated with 1% BSA for 1 hour at 37° C. before being stored at −20° C. For two experiments, plates were also prepared with heat treated or pronase-digested, formalin-killed whole cells. Heat treated cells were prepared by autoclaving for 0.5 hour at 121°–122° C. and 15 PSIG. Pronase treatment was with a 0.1 mg/ml enzyme solution in PBS overnight at 37° C.

Prior to use, the plates were thawed by incubation for 1 hour at 37° C. Wells were washed once with PBS prior to the addition of diluted tissue culture supernatants. All assays were run in duplicate with serial fivefold dilutions of supernatants in PBS containing 0.05% Tween-20 (PBS-T20). After addition of the diluted supernatants the plates were incubated at room temperature for 30 minutes and subsequently washed 3 times with PBS-T20. The assays were completed with reagents from a commercial kit (Vectastain ABC mouse IgG heavy and light chain, Vector Laboratories, Burlingame, Calif.). 50 μl of biotinylated anti-mouse IgG diluted in PBS-T20 was added to each well and plates were incubated at room temperature for 15 minutes before being washed 3 times with PBS-T20. 50 μl of ABC reagent (avidin-biotinylated horseradish peroxidase complex) diluted in PBS-T20 was then added to each well and plates were incubated for 15 minutes at room temperature before 5 washes with PBS-T20. 100 μl of substrate solution consisting of equal parts of 0.03% hydrogen peroxide and 0.8 mg/ml O-phenylenediamine dihydrochloride in 100 mM citrate/phosphate buffer pH 5.3 was then added to each well. After 30 minutes incubation the plates were read at 450 nm using an automated ELISA plate reader. Titers shown are the supernatant dilutions yielding an absorbance value of at least 0.05 above that obtained using a 1:5 dilution of supplemented DMEM in PBS.

RESULTS

Antibody specificity. Seventeen clonal cell lines secreting monoclonal antibodies which reacted with lysates of P. mirabilis 4550 were isolated. Three clonal cell lines were eliminated from further study because their IgM product reacted with or had non-specific affinity for a wide variety of bacterial lysates, including a B. subtilis (gram-positive) lysate. Five additional clonal cell lines were eliminated from further study because their antibody products appeared to react more strongly with P. mirabilis 4550 lysates than with whole cell preparations. Of the nine remaining clonal cell lines, three produced IgG1 antibodies which were broadly cross-reactive among Proteus isolates while six produced IgG1, IgG2b or IgM antibodies which reacted in a serotype-specific manner with P. mirabilis 4550 (Table 1). Surprisingly, when tissue culture supernatants or ascites were tested preliminarily for their capacity to provide in vivo protection, only one (PM-5 VIII-4-F) of the six serotype-specific antibodies was protective against challenge with P. mirabilis 4550. Even more surprising was the observation that the five nonprotective, serotype-specific antibodies were clearly reactive with lipopolysaccharide (LPS) prepared from P. mirabilis 4550 but the protective antibody was not (Table 2.) The literature to date clearly indicates that murine monoclonal antibodies specific for the oligosaccharide determinants of the LPS molecule characterizing a given gram-negative isolate (serotype) are often if not always protective, particularly if the antibody is of a class or subclass which fixes complement (see for example J. Sadoff et al., abstract #253 published on p. 110 of the *Abstracts of the 1982 Interscience Conference on Antimicrobial Agents and Chemotherapy*, M. E. Lostrom et. al., abstract #290 published on p. 136 of the *Abstracts of the 1983 Interscience Conference on Antimicrobial Agents and Chemotherapy*, and T. N. Kirkland and E. J. Ziegler, *J. Immunol.* 132, 2590–2592, 1984). Further evidence indicating that the serotype-specific antibody PM-5 VIII-4-F is not reactive with oligosaccharide determinants of the LPS molecule is shown in Table 3. The determinant recognized by antibody PM-5 VIII-4-F is sensitive to autoclaving and to digestion with pronase, properties not expected of LPS-associated oligosaccharide determinants and not demonstrated by the determinant(s) recognized by the five LPS-reactive, serotype-specific antibodies described here. Finally, it was of interest to note that the protective monoclonal antibody was of the IqG1 isotype and, therefore, most likely does not function through complement-enhanced opsonization (murine IgG1 antibodies, in general, do not fix complement). To our knowledge, the only other protective IgG1 monoclonal described to date for bacterial pathogens (see U.S. Pat. No. 4,443,549) also functions through a unique, non complement-mediated mechanism.

TABLE 2

Monoclonal antibody reactivity (supernatant ELISA titer$^{-1}$) with LPS preparations

| Antibody | Isotype | P. mirabilis 4550 Expt. 1 | P. mirabilis 4550 Expt. 2 | P. aeruginosa F1 Expt. 1 | P. aeruginosa F1 Expt. 2 |
|---|---|---|---|---|---|
| PM-5 II-10-E | IgM | 625 | 625 | —[a] | — |
| PM-5 I-2-F | IgG1 | — | — | — | — |
| PM-5 V-5-F | IgM | 25 | 125 | — | — |
| PM-5 IV-2-C | IgG2b | 625 | 125 | — | — |
| PM-6 XVI-10-C | IgG1 | — | — | — | — |
| PM-6 IX-4-D | IgG2b | 3,125 | 3,125 | — | — |
| PM-5 VIII-5-D | IgG1 | — | — | — | — |
| PM-5 V-7-G | IgM | NT[b] | 625 | NT | — |
| PM-5 VIII-4-F | IgG1 | — | — | — | — |

[a] = where no value is shown, the supernatant titer was <1:5.
[b] = not tested.

TABLE 3

Monoclonal antibody reactivity (supernatant ELISA titer$^{-1}$ with treated P. mirabilis cells

| | P. mirabilis #4550 cells | | |
|---|---|---|---|
| Antibody | Untreated | Heat Treated | Pronase Treated |
| PM-5 II-10-E | 3,125 | 3,125 | 625 |
| PM-5 I-2-F | 125 | 25[a] | —[b] |
| PM-5 V-5-F | 125 | 125 | 3,125 |
| PM-5 IV-2-C | 625 | 3,125 | 15,625 |
| PM-6 XVI-10-C | 25 | 5[a] | — |
| PM-6 IX-4-D | 3,125 | 3,125 | 15,625 |
| PM-5 VIII-5-D | 15,625 | 3,125[a] | — |
| PM-5 V-7-G | 3,125 | 3,125 | 3,125 |
| PM-5 VIII-4-F | 3,125 | — | — |

[a] = reduced signal (ELISA absorbance) relative to untreated cells.
[b] = where no value is given, supernatant ELISA titer was <1:5.

INHIBITION OF MOTILITY

Inhibition of Motility

Direct examination. One drop of fresh P. mirabilis 4550 liquid culture grown at 37° C. was mixed on the surface of a slide with one drop of murine ascites containing the VIII-4-F IgG1 monoclonal reactive with P. mirabilis 4550. As a control, nonimmune ascites was mixed with P. mirabilis 4550 culture. The mixture was covered with a cover slip and examined by light microscopy.

Inhibition of motility in soft agar. To 50 ml of molten motility medium (BBL) was added 0.5 ml of VIII-4-F ascites, control ascites or saline. The agar was poured into culture plates and allowed to harden. In the center

TABLE 1

Monoclonal antibody reactivity (supernatant ELISA titer$^{-1}$) with formalin-fixed whole bacteria

| | Supernatant | | | | | | | | |
|---|---|---|---|---|---|---|---|---|---|
| Bacterial strain | PM-5 II-10-E (M)[a] | PM-5 I-2-F (G1) | PM-5 V-5-F (M) | PM-5 IV-2-C (G2b) | PM-6 XVI-10-C (G1) | PM-6 IX-4-D (G2b) | PM-5 VIII-5-D (G1) | PM-5 V-7-G (M) | PM-5 VIII-4-F (G1) |
| P. mirabilis 4550 | 3,125 | 625 | 625 | 625 | 125 | 3,125 | 15,625 | 3,125 | 625 |
| P. mirabilis 12453 | —[b] | 3,125 | — | — | 3,125 | — | 3,125 | — | — |
| P. mirabilis 25933 | — | 625 | — | — | 625 | — | 3,125 | — | — |
| P. mirabilis 7002 | — | 3,125 | — | — | 3,125 | — | 15,625 | — | — |
| P. vulgaris 13315 | — | 3,125 | — | — | 3,125 | — | 3,125 | — | — |
| P. vulgaris 6380 | — | — | — | — | 5 | — | 3,125 | — | — |
| P. vulgaris 33420 | — | 15,625 | — | — | 15,625 | — | 3,125 | — | — |
| P. vulgaris 8427 | — | 3,125 | — | — | 3,125 | — | 3,125 | — | — |
| M. morganii 25830 | — | 125 | — | — | 625 | — | 3,125 | — | — |
| Y. enterocolitica 23715 | — | — | — | — | — | — | — | — | — |
| P. stuartii 35031 | — | 625 | — | — | 625 | — | — | — | — |
| P. stuartii 33672 | — | — | — | — | — | NT[c] | NT | NT | NT |

[a] = antibody isotypes are shown in parentheses. M = IgM, G1 = IgG1 and G2b = IgG2b.
[b] = where no value is shown, the supernatant titer was <1:5.
[c] NT = Not tested.

of the agar, a loopful of P. mirabilis 4550 was stabbed. The plates were incubated at 37° C. and observed for characteristic P. mirabilis swarming.

Animal protection studies

Inoculum preparation. P. mirabilis 4550, a clinical strain isolated from a leg wound, was maintained in brain-heart infusion broth at −70° C. On the day preceding an animal study, a vial of culture was thawed and subcultured overnight on brain-heart infusion agar. On the day of animal challenge, the overnight culture was subcultured to fresh brain-heart infusion agar slants. After 4 to 5 hours incubation at 37° C., log phase cells were harvested by washing slants with isotonic saline. Cells were washed once and resuspended in saline. Cell concentration in the inoculum was determined by correlating absorption of the suspension at 660 nm with predetermined plate counts. After challenge of mice, the exact number of colony-forming units (cfu) in the inoculum was determined by plate counts on brain-heart infusion agar.

Animal challenge. Dorsal fur of female Swiss-Webster mice weighing 24 to 26 g was clipped from head to tail. Saline dilutions of the PM VIII-4-F ascites were injected intraperitoneally in a 0.1 ml volume. Two to three hours later, mice were anesthetized with an intraperitoneal injection of sodium pentobarbital, 60 to 80 mg/kg body weight. A silica cloth with a 2 by 4 cm oval hole (5.8 cm2) was placed over the back, and mice were given a 10% full thickness burn for 5 seconds with a Fisher gas burner. Inoculum in 0.5 ml of cold saline solution was then injected into the subcutaneous tissue of the burn site. Mice were observed for 15 days following challenge. In one study, at 18 hours after challenge, the skin of the burn site, liver and spleen of mice were removed, homogenized, serially diluted in saline and cultured on MacConkey agar to enumerate P. mirabilis 4550 cfu in tissues.

RESULTS

Inhibition of motility. Cells of P. mirabilis 4550 mixed with VIII-4-F ascites exhibited only Brownian motion when examined by light microscopy. Conversely, cells mixed with non-immune ascites were actively motile. On motility medium containing 1% control ascites or saline, P. mirabilis 4550 exhibited typical swarming. On motility medium containing VIII-4-F ascites, after 18 hours incubation, a 3 to 4 mm colony of P. mirabilis 4550 developed, but no swarming was observed.

Animal protection studies. The mean lethal dose (LD50) of P. mirabilis 4550 in burned mice is approximately 5 cfu. Animals pretreated with 0.1 ml of 1:64 dilution of VIII-4-F ascites resisted a challenge of 1,000 cfu of P. mirabilis 4550 (Table 4). Control ascites were not protective. In mice challenged with 5 LD50 of P. mirabilis 4550, VIII-4-F ascites was protective at a 1:1,024 dilution (Table 5).

Quantitative organ culture of mice treated with saline or a 1:64 dilution of VIII-4-F ascites indicated that the monoclonal prevented proliferation of P. mirabilis 4550 in the burn site and dissemination of the inoculum from the burn site to the liver and spleen (Table 6).

DISCUSSION

For serious infection to occur, a pathogen must disseminate from the site of initial colonization. This is accomplished by elaboration of virulence factors which compromise host defense mechanisms. Several such virulence factors have been described for P. mirabilis. In urine, the enzyme urease degrades urea with the generation of ammonia which may damage urinary tract epithelium and, thus promote serious kidney infection (J. Bacteriol., Vol. 80, pp. 171–79, 1960). When inoculated into rat bladders, heavily piliated strains of P. mirabilis cause ascending pyelonephritis more frequently than lightly piliated strains, presumably by facilitating greater adhesions of cells to the renal pelvis (J. Infect. Dis., Vol. 138, pp. 664–67, 1978). There is considerable evidence to suggest that flagella are also a virulence factor of P. mirabilis. In rats immunized with flagella, immobilizing antibody in the urine prevents homologous, motile P. mirabilis from ascending the ureter to the kidney (Invest. Urology, Vol. 12, No. 2, pp. 129–33, 1974). Also non-motile mutants of P. mirabilis are considerably less virulent in burned rats than motile parent strains (Burns, Vol. 6, pp. 235–39, 1980).

This study indicates that monoclonal VIII-4-F inhibits motility of P. mirabilis and is highly protective in experimental burn wound sepsis. It is noteworthy that treatment with VIII-4-F markedly inhibited proliferation of P. mirabilis 4550 in the tissue of the burn site to the extent that there was 10,000 to 1,000,000-fold fewer cfu in the skin of VIII-4-F treated mice than in control mice (Table 3). Growth of P. mirabilis in motility medium containing antibody VIII-4-F indicates that the antibody is not bacteriostatic or cidal. It is possible that VIII-4-F may function as an opsonin and thus promote phagocytosis, although this was not investigated.

TABLE 4

Effect of anti-Proteus PM-5 VIII-4-F on $LD_{50}$ of P. mirabilis 4550 in burned mice.

| P. mirabilis challenge dose (No. cells) | Cumulative mortality No. dead/total | |
|---|---|---|
| | Saline control | MoAb (1:64 dilution of ascites) |
| 1000 | 5/5 | 0/5 |
| 333 | 5/5 | 1/5 |
| 111 | 5/5 | 0/5 |
| 37 | 5/5 | 0/5 |
| 12 | 5/5 | 1/5 |
| 4 | 2/5 | 0/5 |
| 1 | 1/5 | 0/5 |

TABLE 5

Effect of dilution of PM-5 VIII-4-F ascites fluid on protection afforded burned mice challenged with $5 LD_{50}$ P. mirabilis 4550

| Ascites dilution | Cumulative mortality (No. dead/total) |
|---|---|
| Undil. | 0/5 |
| 1:4 | 0/5 |
| 1:64 | 0/5 |
| 1:1,024 | 2/5 |
| 1:16,384 | 5/5 |
| Saline Control | 10/10 |

TABLE 6
Effect of antibody PM-5 VIII-4-F on growth of *P. mirabilis* in tissues of burned mice

| Mouse number | Cells/g tissue 18 hours after challenge* | | | | | |
|---|---|---|---|---|---|---|
| | Saline control | | | VIII-4-F ascites 1:64 dilution | | |
| | Spleen | Liver | Skin | Spleen | Liver | Skin |
| 1 | $7.0 \times 10^4$ | $2.2 \times 10^4$ | $9.0 \times 10^8$ | 0 | 0 | 0 |
| 2 | $2.3 \times 10^4$ | $1.0 \times 10^4$ | $2.5 \times 10^9$ | 0 | 0 | $5.0 \times 10^3$ |
| 3 | $1.2 \times 10^5$ | $1.3 \times 10^4$ | $1.5 \times 10^9$ | $5.0 \times 10^2$ | 0 | $5.0 \times 10^3$ |
| 4 | $5.0 \times 10^3$ | $1.9 \times 10^2$ | $4.2 \times 10^8$ | 0 | 0 | $2.5 \times 10^4$ |
| 5 | $4.5 \times 10^4$ | $7.7 \times 10^3$ | $2.4 \times 10^9$ | 0 | 0 | $1.7 \times 10^4$ |

*Mice challenged with 65 cells (~15 LD50) in burn site.

Given the above examples, it is thought that numerous modifications and variations will occur to those skilled in the art. Accordingly, it is intended that the above examples should be construed as illustrative only and that the scope of the inventions disclosed herein should be limited only by the following claims.

We claim:

1. Protective monoclonal antibodies specific to a serotypic determinant of a flagellar antigen of the bacerium *Proteus mirabilis* and produced by cell line HB 8879.

2. A method of inhibiting the motility of *Proteus mirabilis* bacteria comprising contacting the bacteria with monoclonal antibodies produced by cell line HB 8879.

3. Cell line HB 8879.

UNITED STATES PATENT AND TRADEMARK OFFICE
CERTIFICATE OF CORRECTION

PATENT NO. : 4,772,464

DATED : September 20, 1988

INVENTOR(S) : RICHARD RUTHERFORD et al.

It is certified that error appears in the above-identified patent and that said Letters Patent is hereby corrected as shown below:

In Claim 1, line 3, "bacerium" should be --bacterium--.

Signed and Sealed this

Seventh Day of February, 1989

Attest:

DONALD J. QUIGG

*Attesting Officer*   *Commissioner of Patents and Trademarks*